(12) United States Patent
Cobanoglu et al.

(10) Patent No.: US 9,861,531 B2
(45) Date of Patent: Jan. 9, 2018

(54) MULTI-FUNCTION EMERGENCY BANDAGE

(71) Applicant: SANKO Tekstil Isletmeleri Sanayi ve Ticaret Anonim Sirketi, Bursa (TR)

(72) Inventors: Ozgur Cobanoglu, Bursa (TR); Jitka Eryilmaz, Bursa (TR); Deniz Sener, Bursa (TR); Mehmet Eryilmaz, Ankara (TR)

(73) Assignee: SANKO TEKSTIL ISLETMELERI SANAYI VE TICARET ANONIM SIRKETI (TR)

( * ) Notice: Subject to any disclaimer, the term of this patent is extended or adjusted under 35 U.S.C. 154(b) by 392 days.

(21) Appl. No.: 13/921,185

(22) Filed: Jun. 18, 2013

(65) Prior Publication Data

US 2014/0371650 A1 Dec. 18, 2014

(51) Int. Cl.
*A61F 15/00* (2006.01)
*A61F 13/00* (2006.01)
(Continued)

(52) U.S. Cl.
CPC .. *A61F 13/00038* (2013.01); *A61F 13/00059* (2013.01); *A61L 15/18* (2013.01);
(Continued)

(58) Field of Classification Search
USPC ............... 602/41–59, 75; 523/105, 111–118; 604/304–308; 424/443, 445, 447
See application file for complete search history.

(56) References Cited

U.S. PATENT DOCUMENTS 5,628,723 A 5/1997 Grau
5,690,610 A * 11/1997 Ito ...................... A61F 13/0203
602/46

(Continued)

FOREIGN PATENT DOCUMENTS

FR 2499416 A * 8/1982
FR 2499416 A1 * 8/1982 ....... A61F 13/00034

OTHER PUBLICATIONS

FR2499416_translation.pdf; machine translation (english) of FR2499416.*

(Continued)

*Primary Examiner* — Ophelia A Hawthorne
*Assistant Examiner* — Caitlin Carreiro
(74) *Attorney, Agent, or Firm* — IP Authority, LLC; Ramraj Soundararajan

(57) ABSTRACT

A unique multi-functional emergency bandage stops bleeding by: (1) optimizing mechanical properties and preventing ischemia and/or necrosis while applying enough pressure to help stop bleeding, and (2) incorporating inorganic anti-bleeding nano-structures (embedded within a gauze and/or microbial cellulose) with almost infinite life-time. Additionally, pathogen passage through the bandage is prohibited (via an intermediate filter layer). Together with the overall anti-microbial character of the bandage, the unique multi-functional bandage offers all these vital features within a single design. The unique bandage can be applied by using a single hand and bandaging direction can be changed using a unique binding apparatus. Visual aids, such as printed rectangles, on the final fabric provides the user with an indication of how to control the amount of stretch, as vertical rectangles would turn into horizontal rectangles when stretched too much, whereas rectangles turn to squares around the optimum region of the stress-strain curve.

15 Claims, 9 Drawing Sheets

(51) Int. Cl.
*A61L 15/44* (2006.01)
*A61L 15/18* (2006.01)
*A61L 15/26* (2006.01)
*A61L 15/42* (2006.01)

(52) U.S. Cl.
CPC .............. *A61L 15/26* (2013.01); *A61L 15/42* (2013.01); *A61L 15/44* (2013.01); *A61F 2013/00106* (2013.01); *A61F 2013/00119* (2013.01); *A61F 2013/00123* (2013.01); *A61F 2013/00463* (2013.01); *A61F 2013/00468* (2013.01); *A61F 2013/00472* (2013.01); *A61L 2300/102* (2013.01); *A61L 2300/418* (2013.01); *A61L 2400/12* (2013.01)

(56) References Cited

U.S. PATENT DOCUMENTS

| | | | |
|---|---|---|---|
| 6,495,087 B1* | 12/2002 | Hwang | B29C 61/0658 156/244.17 |
| 7,462,753 B2 | 12/2008 | Ma et al. | |
| 7,605,298 B2 | 10/2009 | Bechert et al. | |
| 8,025,960 B2 | 9/2011 | Dubrow et al. | |
| 8,237,009 B2 | 8/2012 | Siniaguine | |
| 8,304,595 B2 | 11/2012 | Daniels et al. | |
| 2003/0215522 A1* | 11/2003 | Johnson | A61K 8/27 424/642 |
| 2007/0141130 A1* | 6/2007 | Villanueva | A61L 15/46 424/445 |
| 2007/0203442 A1 | 8/2007 | Bechert et al. | |
| 2010/0081984 A1* | 4/2010 | Coffinardi | A41B 11/126 602/63 |
| 2011/0064785 A1 | 3/2011 | Daniels et al. | |
| 2012/0027681 A1* | 2/2012 | Jung | B82Y 40/00 424/9.1 |
| 2012/0064145 A1 | 3/2012 | Lin et al. | |
| 2012/0107592 A1* | 5/2012 | Vasilev | A61F 13/00017 428/220 |

OTHER PUBLICATIONS

WIA Wounded Areas, Unclassified Army document, Mar. 19, 2003, 3pgs.

* cited by examiner

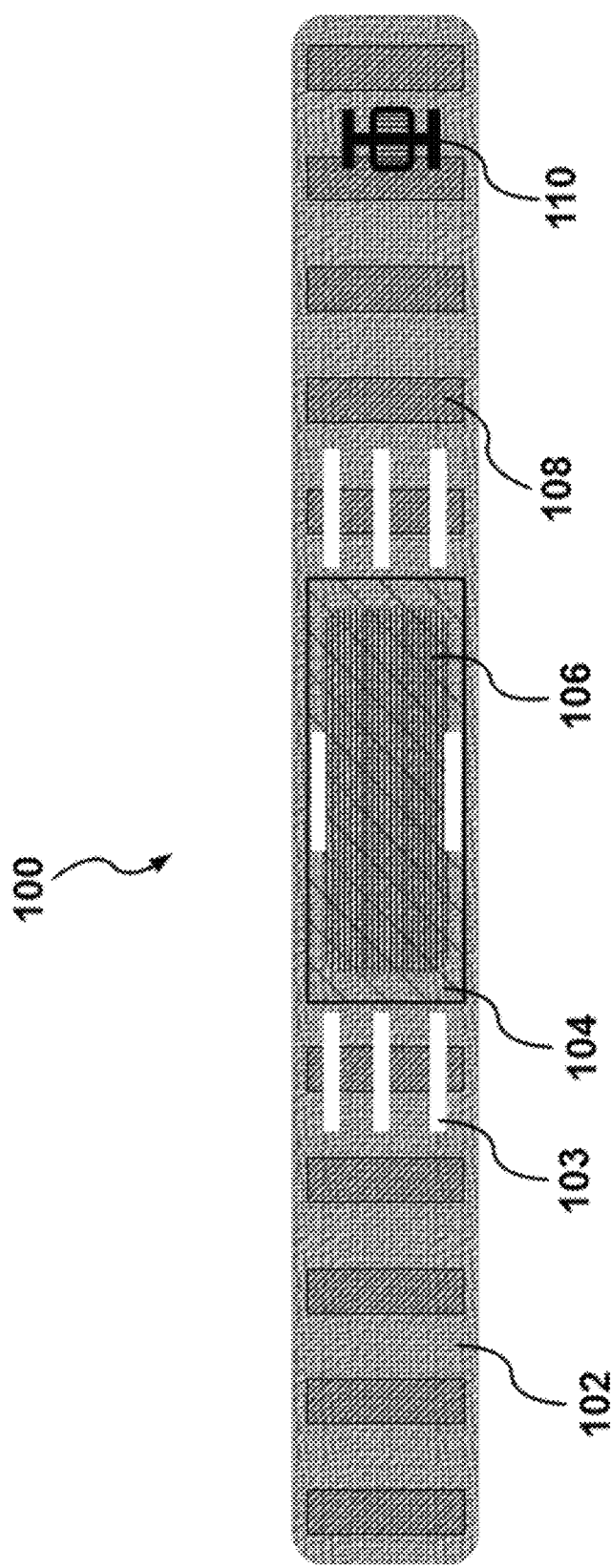

MULTI-FUNCTION EMERGENCY BANDAGE

BACKGROUND OF THE INVENTION

Field of Invention

The present invention relates generally to the field of medical bandages. More specifically, the present invention is related to a unique multi-functional bandage in pre-hospital emergency situations such as civilian condition, disaster, conflict area, warfare and other military applications that target uncontrolled bleeding while preventing ischemia, inflammations, necrosis, pathogen and toxic substrate passage through the bandage.

Discussion of Prior Art

Currently, there are a variety of bandages available on the market to be used in pre-hospital and hospital emergency situations as a first-aid device to stop bleeding from hemorrhagic, amputate or crush wounds caused by traumatic injuries. In recent years, trauma-related mortality of 58% in warfare is due to extremity (e.g. arms, legs, head) injuries as reported in "WIA wounded areas" published unclassified by the U.S. Army on 19 Mar. 2003-18 May 2004. The applicators in the field, therefore, appreciate a bandage—additionally to other functions disclosed here in this application—having the capability of taking the shape of the body and immobilize itself once placed over the wounded area without extra support. This would make it easier—if not possible—to start bandaging with one-hand especially in the following hard-to-bandage areas besides the extremities: axillar, inguinal, buttock, abdominal, and thoracic areas.

However, only a limited percentage of these bandages are available for pre-hospital emergency situations such as accidents, falling down, catastrophic disaster, conflict area, occupational accident and warfare. More particularly, such prior art bandages suffer from at least one of the following shortcomings, if not all:

1. the prior art bandages fail to optimize physical properties of the construction of the bandage fabric by means of stress-strain curves, and as a results of the lack of such optimization, majority of the bandages on the market either cannot stop bleeding or, in case they do, cause ischemia and/or necrosis due to overpressure;

2. the prior art bandages are often impractical as majority of the bandages on the market today are formed by discrete pieces, requiring such discrete pieces to be assembled together by either a single user utilizing both his/her hands or by two users;

3. the prior art bandages lack a mechanism that offers bio-protection of the wound from the environment as none of the emergency bandages available on the market today can properly isolate the wound from a variety of pathogens, such as microbes and/or viruses;

4. the prior art bandages also lack an optimal mechanism to help stop bleeding as majority of the bandages on the market today do not employ mechanisms promoting blood clotting, as such prior art bandages prevent bleeding by merely applying pressure, which is problematic as mentioned previously in bullet item (1); even in the few cases that have mechanisms to promote blood clotting, such mechanisms are limited to organic substances, which is a contributing factor to limiting the life time of such a bandage.

5. the prior art bandages lack elastic immobilization stripes around the wound dressing, making it difficult for one-handed application, which renders vital in the field.

6 none of the prior art bandages has optimized and unified all three functions in a single design such as optimization of i) physical properties by means of stress-strain curve and anti-slip stripes, ii) addition of anti-microbial chemical properties, iii) together with incorporating biological properties of pathogen and harmful substrate blocking/trapping as well as of contributing factor to stop bleeding.

The following references are all representative of the prior art mentioned above and suffer from the shortcomings mentioned above.

The patent application to Grau (U.S. Pat. No. 5,628,723) discloses an emergency bandage with an apparatus allowing the user to apply pressure onto the wound and change the bandaging direction abruptly by a single hand.

The patent to Ma et al. (U.S. Pat. No. 7,462,753) provides for a nano-silver wound dressing. In Ma et al., the dressing comprises a skin contact layer, a disinfected antitoxic layer of activated charcoal cloth impregnated with nano-crystalline silver, an isolation layer of a composite fabric having a very small pore size that provides a barrier to bacterial penetration, and an elastic bandage.

The patent to Bechert et al. (U.S. Pat. No. 7,605,298) provides for a Wound Covering. In Bechert, the wound covering comprises an absorbent matrix of non-woven material having nano-scale silver that contacts the wound and a gas-permeable, liquid impermeable layer 14.

The patent to Dubrow et al. (U.S. Pat. No. 8,025,960) provides for porous substrates, articles, systems and compositions comprising nano-fibers and methods of their use and production. In Dubrow et al., the bandage comprises a flexible porous substrate strip having a nano-fiber coating (wherein the nano-fibers comprises antimicrobial materials, such as ZnO) and a protective pad which provides the contact surface for the wound.

The patent to Daniels et al. (U.S. Pat. No. 8,304,595) provides for a resorbable nano-enhanced hemostatic structures and bandage materials. In Daniels et al., the bandage comprises bandage material and nanoparticles which are provided to assist clotting and slow down the bleeding.

The patent application publication to Villanueva et al. (US 2007/0141130) provides for a wound or surgical dressing. In Villanueva et al., the bandage comprises a base layer of non-woven sheet or film and a substrate, such as an absorbent pad, positioned in the center of the base layer, the pad having a bacteriostatic composition applied thereto to trap bacteria, pathogens, microbes, etc., wherein the bacteriostatic composition may be an ammonium salt that is embedded within the fibers of the pad.

The patent application publication to Lin et al. (US 2012/0064145) provides for a Wound Dressing. In Lin et al., the double-layer wound dressing comprises an outer polymer material layer containing antibacterial material 11 to function as a bacterial barrier, and a porous carbon material layer having epithelial cells therein to promote wound healing.

The patent to Siniaguine (U.S. Pat. No. 8,237,009) discloses a wound covering comprising a topmost dressing layer fabricated of a non-woven mesh of polymer microfibers and a second layer of non-woven microfiber mesh having a very small pore size sufficient to form a microbe impermeable layer.

The patent application publication to Jung et al. (US 2012/0027681) discloses utilizing carbon nanostructures to deliver a target agent, such as sialic acid, which can be used to target various viruses.

The patent application publication to Vasilev et al. (US 2012/0107592) discloses using copper, silver or gold nanoparticles in a wound dressing.

Whatever the precise merits, features, and advantages of the above cited references, none of them achieves or fulfills the purposes of the present invention.

SUMMARY OF THE INVENTION

The present invention discloses a multi-functional emergency bandage comprising: a base layer comprising an elastic textile fabric coated with anti-microbial nano-structures, wherein physical properties of said base layer is optimized using a stress-strain curve to both prevent ischemia and/or necrosis and stop bleeding; an intermediate layer filtering pathogens; and a gauze and/or microbial cellulose that is decorated with anti-bleeding nano-structures. Such a multi-functional emergency bandage may further comprise a plurality of printed geometric shapes disposed on the base layer, wherein an aspect ratio associated with each of the geometric shapes changes as an indication of how much the bandage is stretched corresponding to a calibrated stress. Such a multi-functional emergency bandage may further comprise a binding apparatus disposed on said base layer allowing either a one-handed application of the multifunctional emergency bandage or an abrupt change in bandaging direction. One handed application is further facilitated by the addition of silicone stripes surrounding the wound dressing in order to increase the friction coefficient between the bandage and the tissue.

The present invention also discloses a multi-functional emergency bandage comprising: a base layer comprising an elastic textile fabric coated with anti-microbial nano-structures, wherein physical properties of said base layer is optimized using a stress-strain curve to both prevent necrosis and stop bleeding, said base layer having a calibrated display disposed thereon; an intermediate layer filtering pathogens; and a gauze and/or microbial cellulose that is decorated with anti-bleeding nano-structures, wherein an aspect ratio associated with a geometric shape viewable within said calibration display changes as an indication of how much the bandage is stretched corresponding to a calibrated stress.

The present invention also discloses a multi-functional emergency bandage comprising: a base layer comprising an elastic textile fabric coated with anti-microbial nano-structures, wherein physical properties of said base layer is optimized using a stress-strain curve to both prevent necrosis and stop bleeding, said base layer having a plurality of printed geometric shapes are disposed thereon; an intermediate layer filtering pathogens; and a gauze and/or microbial cellulose that is decorated with anti-bleeding nano-structures, wherein an aspect ratio associated with each of the geometric shapes changes as an indication of how much the bandage is stretched corresponding to a calibrated stress.

In one embodiment, the strength and slope of said stress-strain curve are maintained around an optimum region such that the multi-functional emergency bandage applies required pressure onto a wound to help stop bleeding while preventing ischemia and/or necrosis due to potential overpressure.

In one embodiment, the strength of said fabric is fixed around an optimum region associated with the stress-strain curve associated with said fabric material, such that the multi-functional emergency bandage applies required pressure onto a wound to help stop bleeding while preventing necrosis due to potential overpressure.

In one embodiment, the slope of said stress-strain curve is set small so that pressure said multi-functional bandage applies onto a wound is a weak function of how much it is stretched but a strong function of how many times it wraps around said wound.

In one embodiment, the anti-microbial nano-structures in the base layer are any of the following: quaterne ammonium nano-swords, metal nano-particles (e.g., silver or gold nano-particles), and antimicrobial oxides (e.g., $TiO_2$ and ZnO).

In one embodiment, the anti-bleeding nano-structures in the gauze and/or microbial cellulose comprises any of the following: natural minerals known as double salts (e.g., $KNa_{46.72}Ca_3Mg_{1.305}Al_{69.46}HSi_{86.1}S_{42}O_{431}$ $nH_2O$), synthetic platelets and amino acids sequences.

In one embodiment, the intermediate layer is decorated with microbial and/or viral pathogen blocking structures wherein said microbial and/or viral pathogen blocking structures comprises any of the following: polymer chains containing sialic acid and a sialic acid derivative.

In one embodiment, the base layer around the wound dressing gauze has coated elastic silicone stripes in order to establish high friction coefficient between the bandage and the tissue helping immobilization of the bandage at the initial stage of the application.

BRIEF DESCRIPTION OF THE DRAWINGS

FIGS. 1A-B and FIGS. 1C-D illustrate two structures associated with two embodiments of the present invention.

DESCRIPTION OF THE PREFERRED EMBODIMENTS

Figure 1B:
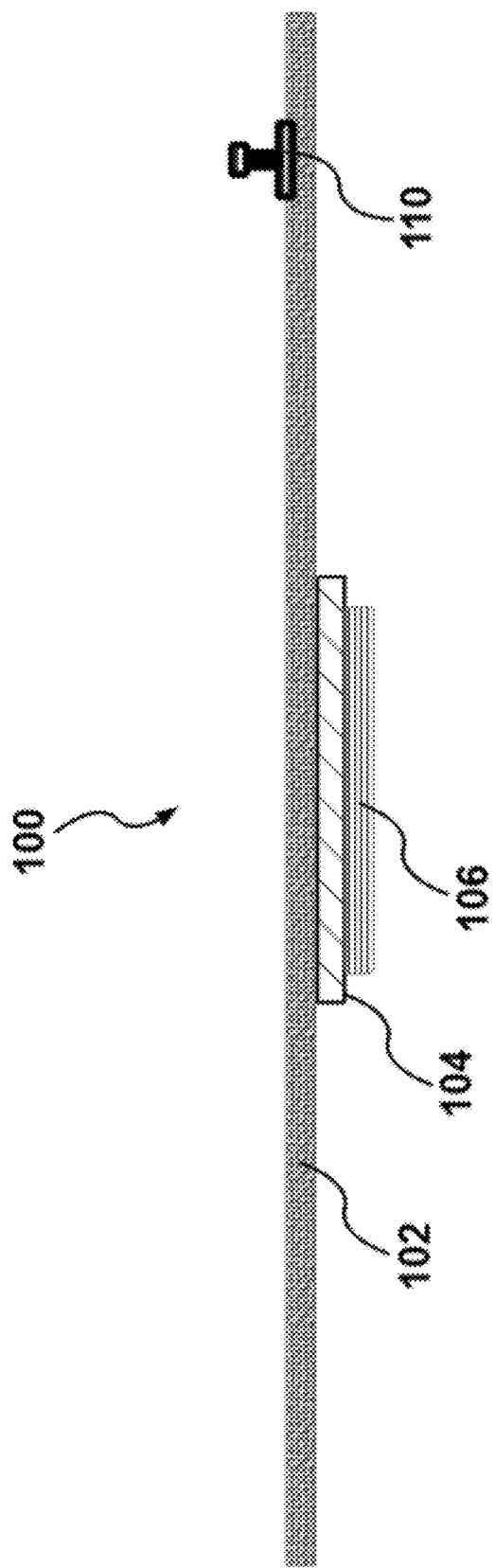

While this invention is illustrated and described in a preferred embodiment, the device may be produced in many different configurations, forms and materials. There is depicted in the drawings, and will herein be described in detail, a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the present invention.

FIG. 1A, FIG. 1B, FIG. 1C and FIG. 1D depict two embodiments of the present invention's bandage 100.

Figure 2D:
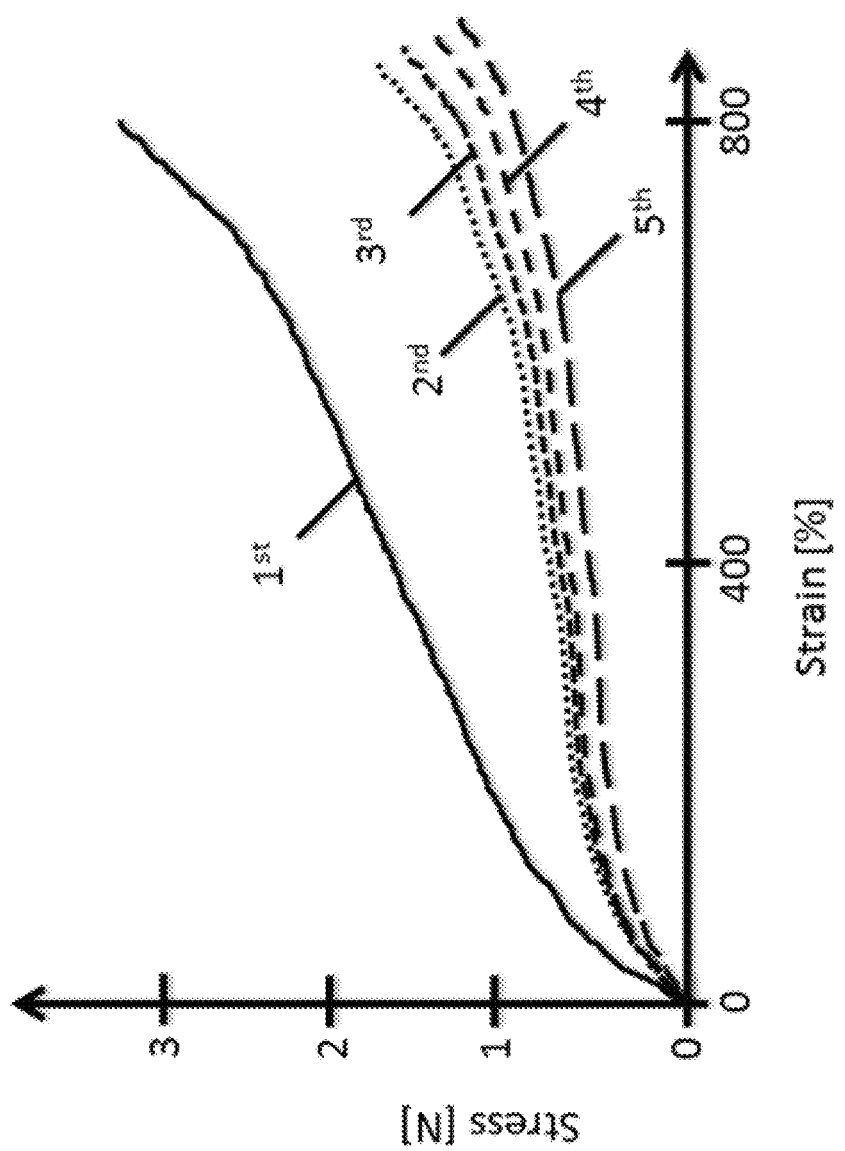
FIG. 2D illustrates stress-strain curves measured on a single fiber where the solid line is the measurement of the first run exhibiting a high modulus, whereas the dashed ones are those after the first run, showing the intrinsic fatigue behavior of the elastomeric fiber, exhibiting a lower modulus.
Figure 3:
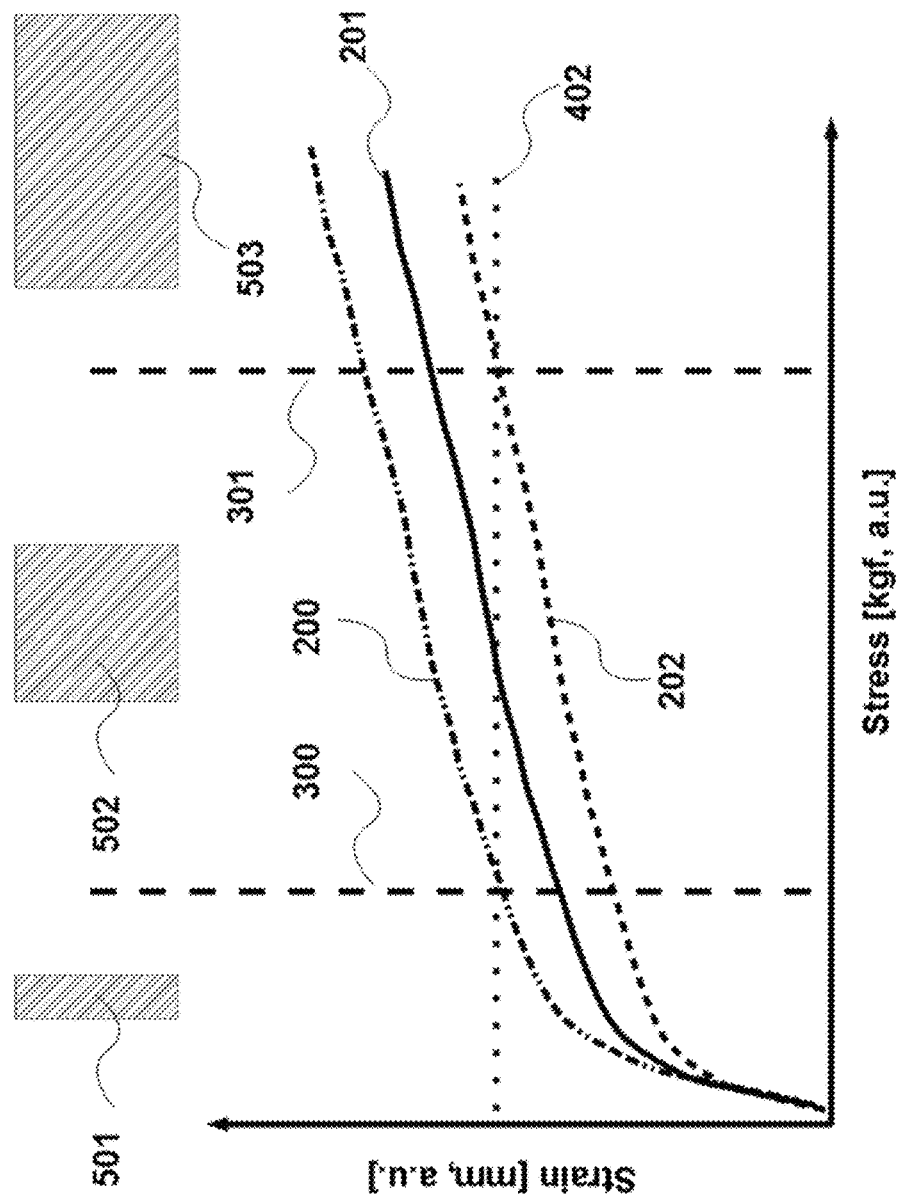
FIG. 3 illustrates a comparison of stress-strain curves for picking the optimal properties associated with the present invention's bandage structure.

In the first embodiment, as shown in FIG. 1A-B, bandage 100 comprises the following layers: a base layer 102 comprising an elastic textile fabric that is coated with anti-microbial nano-structures and with optimized physical properties (i.e., optimized in relation to a stress-strain curve) as well as coated with elastic silicone stripes 103 around the wound dressing gauze to immobilize the bandage to the tissue; an intermediate layer 104 that functions as a filter to trap and block various pathogen families; and gauze and/or microbial cellulose 106 that is decorated with anti-bleeding nano-structures. The multi-functional emergency bandage may further comprise a binding apparatus 110 disposed on the base layer 102 allowing either a one-handed application of the multifunctional emergency bandage or an abrupt change in bandaging direction. In one embodiment, base layer 102 is woven. In another embodiment, base layer 102 is accompanied by elastomers such as lycra and/or structures containing synthetic yarns made of polyamide and polyurethane, many of which are knitted rather than woven. These offer considerable advantages over their predecessors, being more conformable (and thus easier to apply) as well as more elastic due to the use of new elastomeric yarns. Bandages applied with excessive tension as a consequence cause tissue damage leading to necrosis. Therefore, the safe application of the bandage is achieved by introducing geometrical shapes 108 as visual aids printed throughout the bandage on the base layer, wherein an aspect ratio associated with each of the geometric shapes 108 changes as a function of how much the bandage is stretched. Base layer 102 is further facilitated by the presence of a printed geometrical shapes 108 consisting of a rectangular shape that changes to a square when the bandage is extended to the optimum working range of 60-80 mm Hg. The optimum working range is derived based on many clinical trial studies where a certain amount of pressure is applied to the wound to control bleeding without constricting normal circulation and maintaining oxygen delivery to the tissues. Most literature suggests that a pressure of about 70 mm Hg is necessary to nearly occlude the deep femoral veins. Therefore, the bandage fabric tension is pre-programmed into the product during the manufacturing process and calibrated to achieve the 60-80 mm Hg of applied pressure range after certain number of turns. Additionally, the total pressure the bandage applies is made a weak function of the flexing (i.e., how much it flexes) but is a strong function of the number of turns the user applies. Weak function is a function where the result does not change significantly when the dependent variable changes. On the contrary, a strong function or a heavily dependent function changes significantly even when the variable on which the function is based varies slightly. As examples $f(x)=x+1$ is a much weaker function of x compared to $g(x)=x^2$ due to the fact that for a given variation in dependent variable "x", g changes much more then f. This is achieved by physical pre-aging of the elastic fibers within the fabric construction as seen in FIG. 2D where the solid line shows a measured stress-strain characteristic of an elastomeric fiber at the first test cycle and the other dotted/dashed ones each are those after the first test cycle, representing a consistent and lower Young's modulus. The geometrical shapes 108, spread throughout the bandage, will visually help to guide the user on how to apply the bandage correctly as depicted in FIG. 3.

Figure 1C:
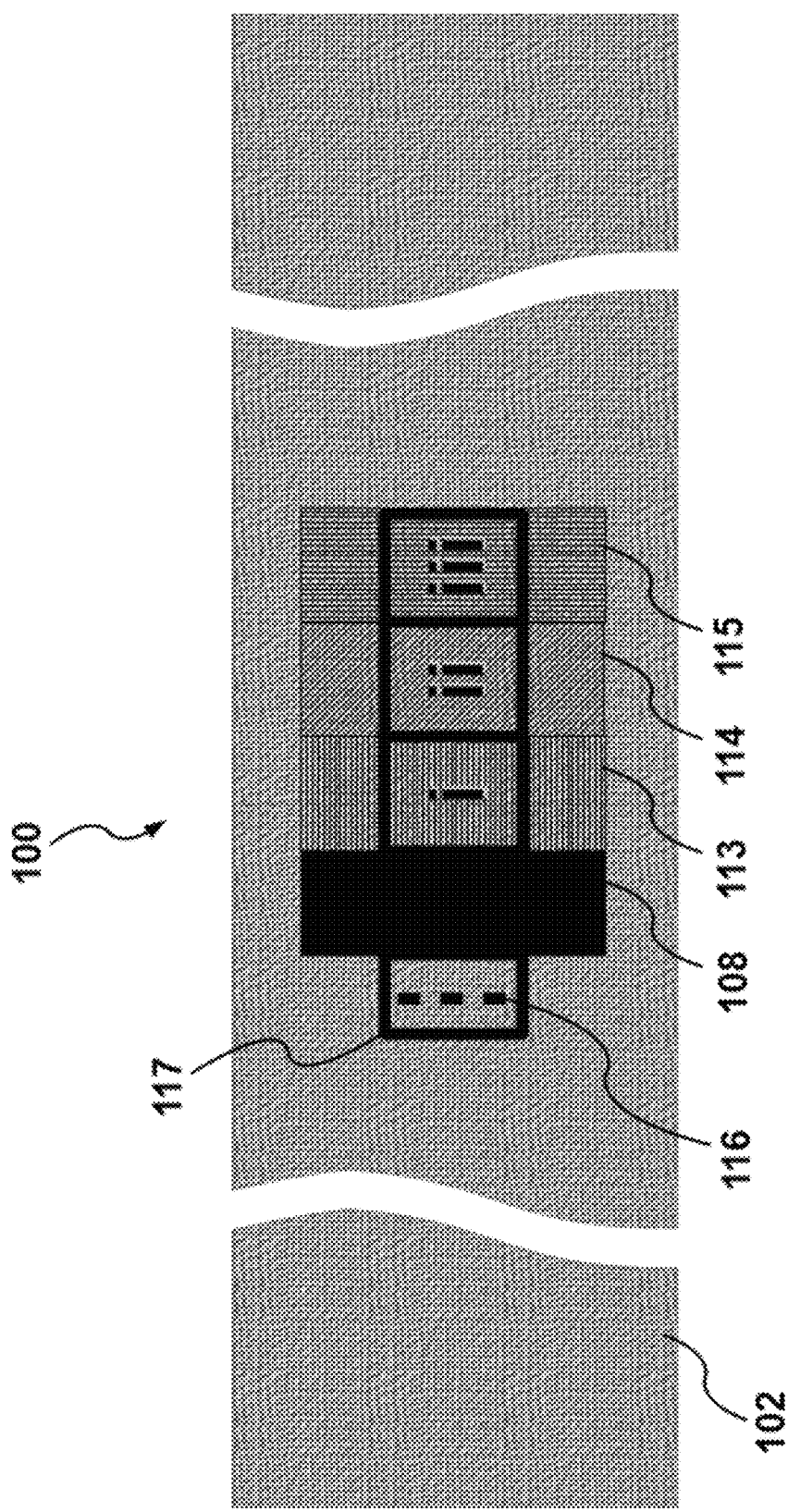
Figure 1D:
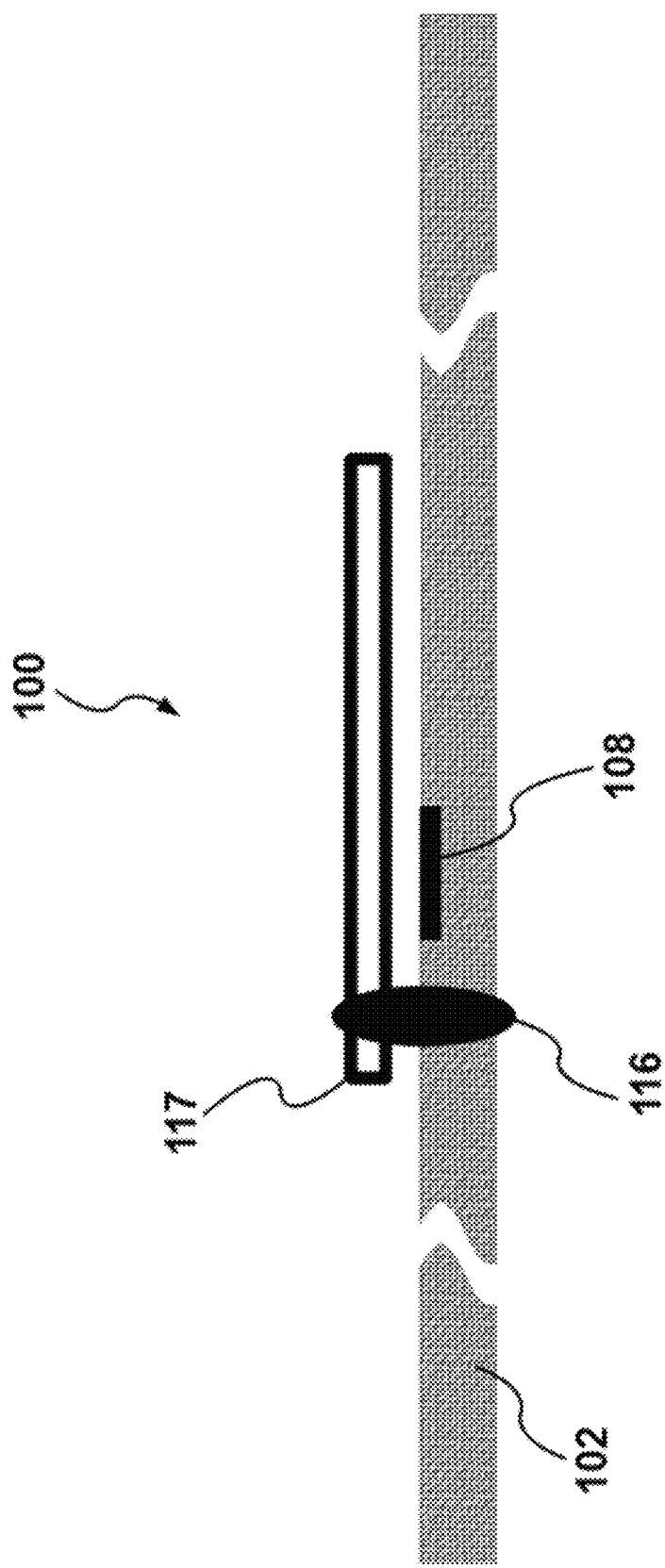

Another embodiment as shown in FIG. 1C-D utilizes a small transparent display to better control the amount of pressure the bandage applies. In this embodiment, the tension of the fabric will be calibrated in the following manner: as the printed rectangular shape 108 is stretched to cover the area denoted by 113, the user will understand that the strain under this much strain is 100%, which corresponds to a certain amount of pressure to the wound. Similarly, the stretch of 108 to cover the area denoted by 114, gives 200% etc., which helps the user to achieve the right amount of pressure per turn, say 10 mm Hg per an additional 100% extension and per turn. Similarly, the stretch of geometric shape 108 to cover the area denoted by 115, gives 300% strain. Therefore, the user can apply pressure on the wound accurately and precisely. A transparent piece of plastic 117 may be used as a calibration meter holding the printed numbers "i", "ii", and "iii". Stitch 116 holds the transparent piece of plastic 117 on the fabric. FIG. 1C is a detail of the same embodiment of the emergency bandage. FIG. 1C does not show the bandage structure (as shown in FIG. 1A-B, but represents a visual aid for the user to better control the amount of bandage strain, where the visual aid is somewhere other than the wound dressing part.

The present invention optimizes the physical properties of the construction of the bandage by optimizing its stress-strain behavior. This is accomplished via changing the construction of the fabric that the base layer 102 is formed of, which is formed by various types of fibers each having a different function, by means of fiber cross-sections and their numbers as well as the way the fabric is woven.

The present invention's bandage structure does not allow bacteria to localize on and populate within the bandage matrix, as it uses anti-microbial nano-structures in base layer 102 wherein such anti-microbial nano-structures may be any one of, but not limited to, the following: quaterne ammonium nano-swords, metal nano-particles such as silver and gold, antimicrobial oxides such as $TiO_2$ and ZnO, natural minerals, wherein such anti-microbial nano-structures kill the bacteria via destroying cell-walls of a variety of bacteria both Gram+ and Gram−.

The present invention's bandage structure prevents pathogen transfer in both directions through the bandage in order to microbially and virally isolate the wounded region from the environment by trapping and immobilizing them using the intermediate layer 104. Bacteria and viruses infect the human cells via first interacting with sialic acid (SA) terminated polymer chains (PC) decorating the surface of the human cell and using those as handles to attach onto. Trapping uses the same idea to mimic the surface properties of human cells on textile fabrics in order to trap and immobilize such pathogens.

The present invention's bandage structure also helps halt bleeding by using commercially available products, chemicals or nano-structures embedded within gauze and/or microbial cellulose 106 such as WoundSeal, these products contain hydrophilic polymer and a potassium salt. Together, they work to form an artificial scab over minor cuts. Seal-On products contain cellulose and also work by forming a gel-like layer over the cut. QuikClot® products are made with a natural mineral called zeolite. Zeolite accelerates the body's natural clotting mechanism to create a clot. BloodSTOP® product is made of plant cellulose. When BloodSTOP® comes in contact with blood, it forms a clear gel that seals the wound with a protective transparent layer. Celox™ granules are large surface area flakes and as they come in contact with blood, they swell, gel, and stick together to make a gel like clot, which plugs the bleeding site. Other products such as natural minerals, synthetic platelets and/or amino acids can be used within the gauze and/or microbial cellulose 106 to stop the bleeding. The double salts containing ions of the following elements: Al, Ca, K, Mg, Na, Si, S (such as $KNa_{46,72}Ca_3Mg_{1,305}Al_{69,46}HSi_{86,1}S_{42}O_{431} \cdot nH_2O$) can be used as well.

The present invention's bandage structure is further decorated with elastic silicone stripes 103 surrounding the wound dressing gauze in order to increase the high friction coefficient between the bandage and the tissue helping immobilization of the bandage at the initial stage of the application, which renders vital for the survival. This anti-slip function allows one to better control the following bandaging turns.

Figure 2A:
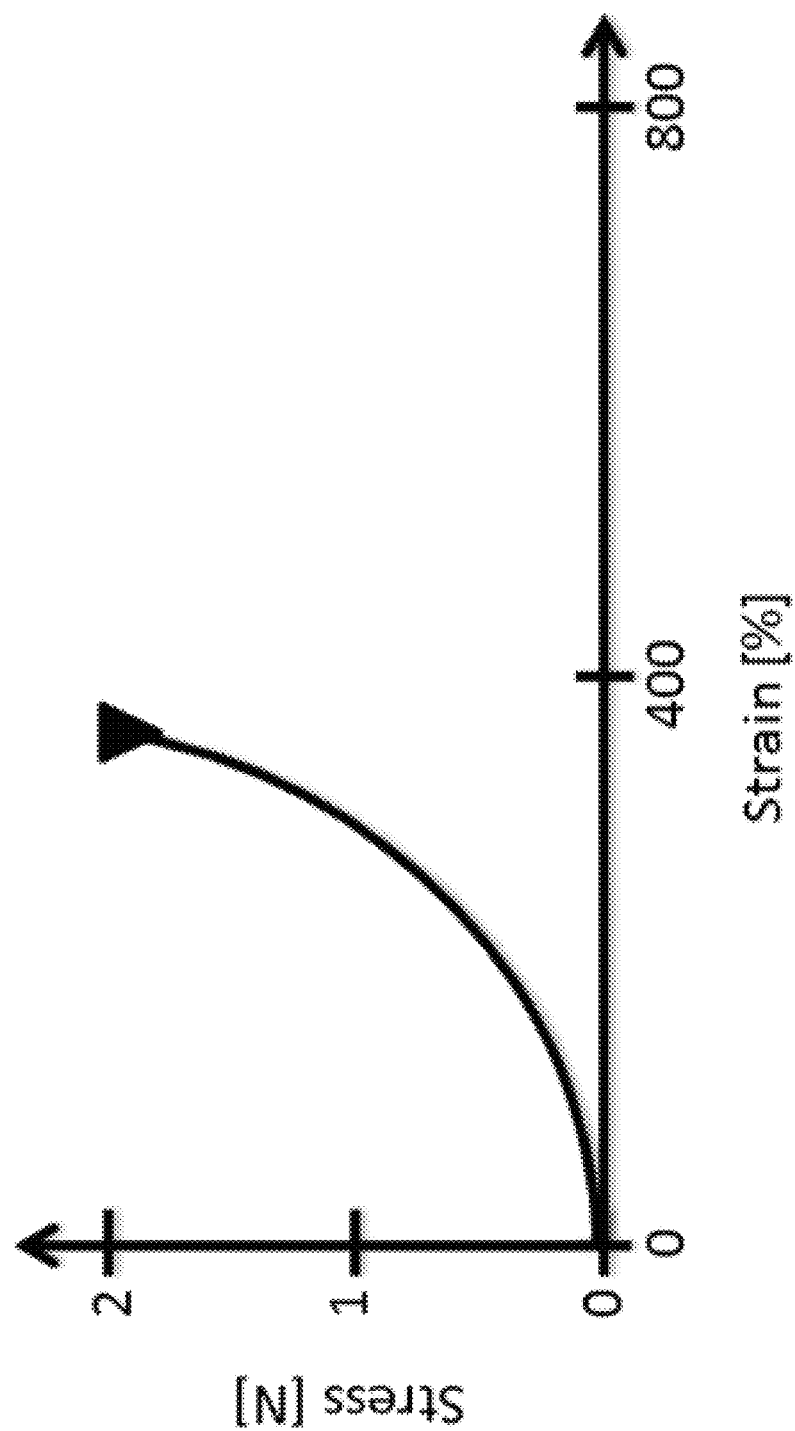
FIGS. 2A through 2C illustrate various stress-strain curves in commercially available bandages (FIGS. 2A and 2B) as compared with stress-strain curve of a non-limiting example of a bandage made in accordance with the teachings of the present invention.
Figure 2B:
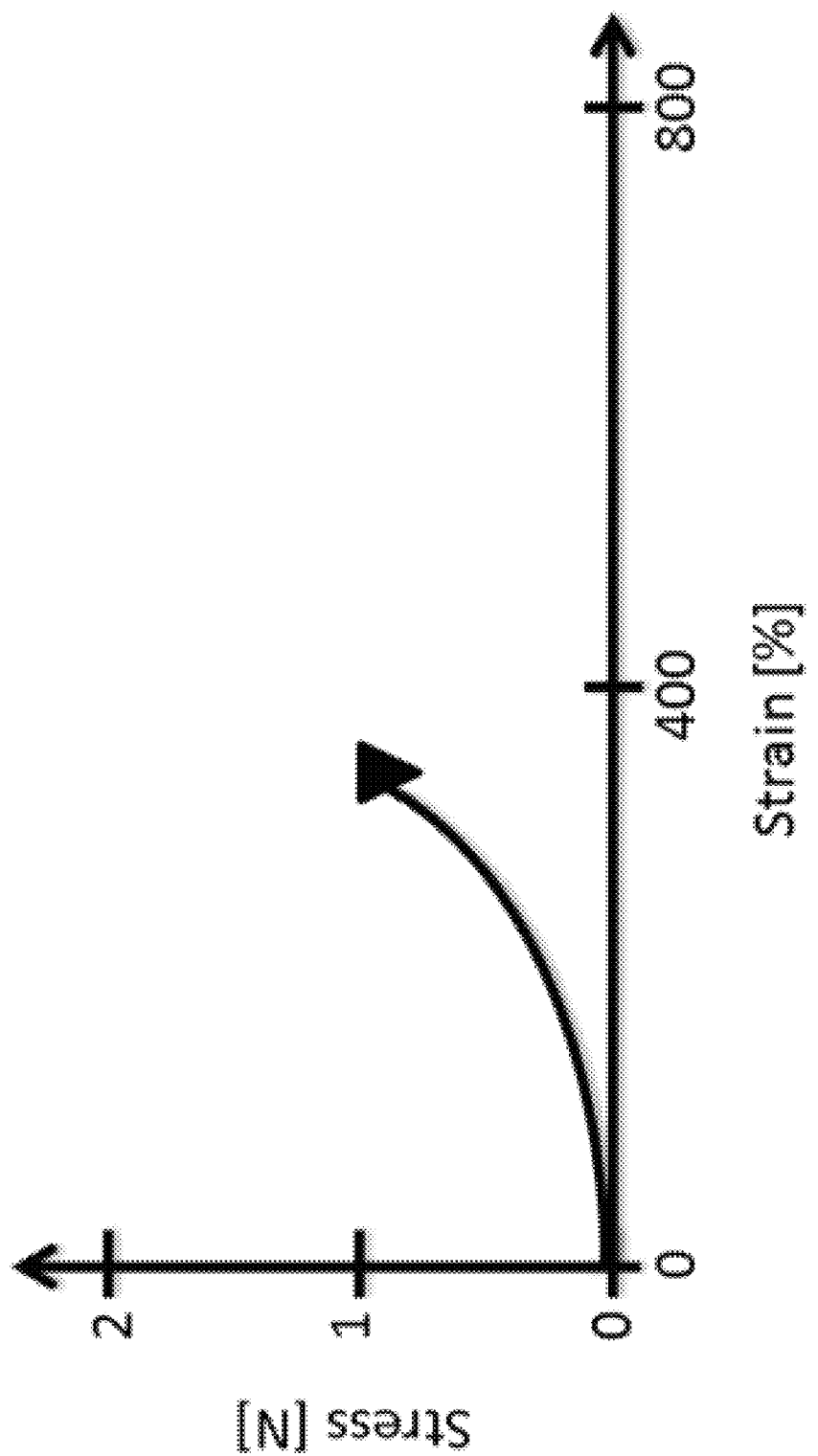
Figure 2C:
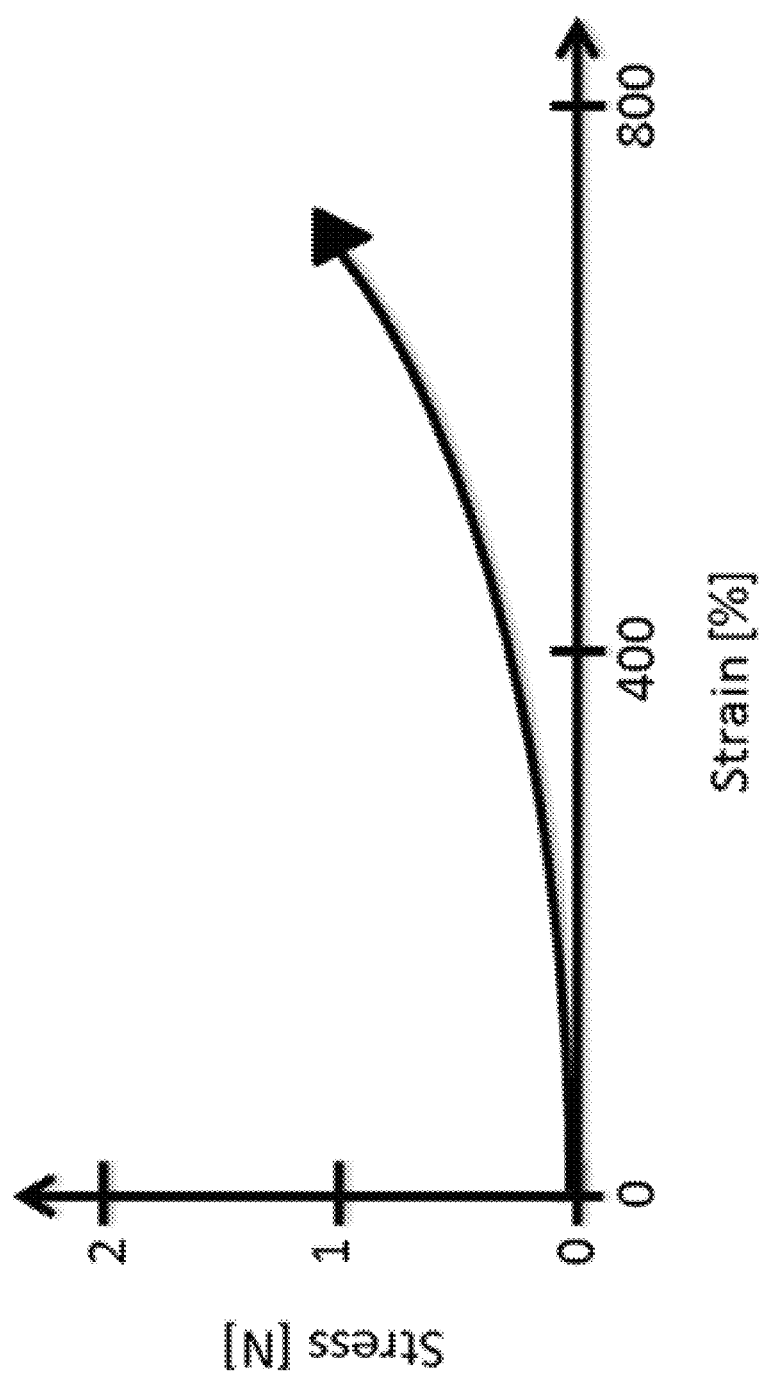

FIG. 2A through FIG. 2C illustrate the measured stress-strain curves of single fibers with different chemical properties which are commercially available (FIG. 2A and FIG. 2B) and the one which is employed in the bandage disclosed in this application (FIG. 2C). Given a specific fabric design and amount of strain, an emergency bandage made out of fibers, of which the stress-strain curve is given in FIG. 2A, might cause necrosis due to excessive force it applies. On the other hand, that of FIG. 2B would not even sustain the stretch required as its breaking point is much lower. Additionally, that of FIG. 2B might fail to stop bleeding due to not enough stress being applied. Whereas, the one depicted in FIG. 2C can be used due to its larger expansion range and its low modulus, allowing the present invention to make the pressure the bandage applies a weak function of how much it expands but a strong function of how many turns the user applies.

FIG. 2D depicts a graph of stress versus strain measured during the process of physical pre-aging of the elastic fibers within the fabric construction, where the solid line shows a measured stress-strain characteristic of an elastomeric fiber at the first test cycle and the other dotted/dashed ones each are those after the first test cycle, representing a consistent and lower Young's modulus. The solid line (labeled "$1^{st}$") is the first cycle of the stress-strain measurement whereas the others, starting from the top of the group, are those measured consecutively after the first one, all belonging to the same sample. During the first measurement, the sample age and, therefore, the other curves go down and their modulus decreases as a result of this aging. The curves shift downward and to the right. The former is due to weakening of the fiber and the latter is due to the fact that the sample is not removed from the sample holder. Therefore, the x-axis expands due to calibration loss as the fiber elongates. A low Young's modulus is desirable. As the fiber is aged just by elongating it once during the fabrication, a lower modulus is attained and its behavior is more stable. That is, the difference between the $1^{st}$ and $2^{nd}$ curves is much larger as compared to the $2^{nd}$ and the $3^{rd}$ ones. Therefore, it is desired to characterize the final product with the lower curves.

FIG. 3 depicts a comparison of stress-strain curves of three different bandages: weak, optimum and strong, denoted as 200, 201, and 202, respectively. For a given strain denoted as 402, the weak bandage 200 cannot apply enough stress (a condition shown by dotted vertical line 300) leading to continued blood loss whereas the strong bandage 202 applies too much pressure causing necrosis (a condition shown by dotted vertical line 301). The optimum is considered to be somewhere in-between the two extreme conditions denoted as 201. Considering a single stress-strain curve, say, associated to that of optimum bandage 201 where the weak region geometric shape 501, optimal region geometric shape 502, and overpressure region geometric shape 503 exhibit the expected aspect ratios of the printed geometric shapes corresponding to weak (bleeding does not stop), optimum, and overpressure (ischemia and necrosis) regions. Such values are taken from the publications where the conclusion on pressure ranges for optimal blood stopping is extracted by controlled experiments on animals and clinical trials on healthy volunteers (see, for example, the paper to S. Thomas in the EMWA Journal titled "The Use of the Laplace Equation in the Calculation of Sub-Bandage Pressure" and the paper to Logan et al. published in the Journal of Wound Care titled "A Comparison of Sub-Bandage Pressures Produced by Experienced and Inexperienced Bandagers").

CONCLUSION

A system and method has been shown in the above embodiments for the effective implementation of a multi-function emergency bandage. While various preferred embodiments have been shown and described, it will be understood that there is no intent to limit the invention by such disclosure, but rather, it is intended to cover all modifications and alternate constructions falling within the spirit and scope of the invention, as defined in the appended claims. For example, the present invention should not be limited by size, materials, or specific manufacturing techniques.

The invention claimed is:

1. A multi-functional emergency bandage comprising:
a base layer comprising an elastic textile fabric: (i) coated with anti-microbial nano-structures, and (ii) with one or more anti-slip stripes, wherein the base layer comprises pre-aged elastic fibers that are pre-aged by elongation, the pre-aged elastic fibers exhibiting a fatigue behavior and providing the base layer with physical properties such that its stress-strain curve exhibits a lower and more consistent Young's modulus, at least over a working range of said stress-strain curve, compared to a base layer without pre-aged elastic fibers;
an intermediate layer filtering pathogens; and
a gauze and microbial cellulose that is decorated with anti-bleeding nano-structures.

2. The multi-functional emergency bandage of claim 1, further comprising a plurality of printed geometric shapes disposed on said base layer, wherein an aspect ratio associated with each of the geometric shapes changes as an indication of how much the bandage is stretched, corresponding to a calibrated stress.

3. The multi-functional emergency bandage of claim 2, further comprising calibration displays that are disposed on said base layer, wherein said geometric shapes change to a first pre-determined shape at a first stress level and to a second pre-determined shape at a second stress level, said first and second stress level corresponding to an applied pressure value picked between 60-80 mm Hg.

4. The multi-functional emergency bandage of claim 1, further comprising calibration displays disposed on said base layer, wherein an aspect ratio associated with a geometric shape viewable within said calibration display changes as an indication of how much the bandage is stretched corresponding to a calibrated stress.

5. The multi-functional emergency bandage of claim 1, wherein strength and slope of said stress-strain curve are maintained around an optimum region such that the multi-functional emergency bandage applies required pressure onto a wound to help stop bleeding while preventing necrosis due to potential overpressure.

6. The multi-functional emergency bandage of claim 1, wherein strength of said fabric is fixed around an optimum region associated with the stress-strain curve associated with said fabric, such that the multi-functional emergency bandage applies required pressure onto a wound to help stop bleeding while preventing necrosis due to potential overpressure.

7. The multi-functional emergency bandage of claim 1, wherein said anti-microbial nano-structures are any of the following: quaterne ammonium nano-swords, metal nano-particles, and antimicrobial oxides.

8. The multi-functional emergency bandage of claim 1, wherein said anti-microbial nano-structure comprises metal nanoparticles selected from the group consisting of: silver or gold.

9. The multi-functional emergency bandage of claim 1, wherein said anti-microbial nano-structure comprises anti-microbial oxides selected from the group consisting of: $TiO_2$ and ZnO.

10. The multi-functional emergency bandage of claim 1, wherein said anti-slip stripes comprise silicon rubber based mixtures or silicone derivatives.

11. The multi-functional emergency bandage of claim 1, wherein said anti-bleeding nano-structures comprises any of the following: natural minerals known as double salts, synthetic platelets and amino acids.

12. The multi-functional emergency bandage of claim 11, wherein said double salt is $KNa_{46,72}Ca_3Mg_{1,305}Al_{69,46}HSi_{86,1}S_{42}O_{431}$ $nH_2O$.

13. The multi-functional emergency bandage of claim 1, wherein said intermediate layer is decorated with any of the following: microbial or viral pathogen blocking structures.

14. The multi-functional emergency bandage of claim 13, wherein said microbial or viral pathogen blocking structures comprise any of the following: polymer chains containing sialic acid and a sialic acid derivative.

15. A multi-functional emergency bandage comprising:
   a base layer comprising an elastic textile fabric: (i) coated with anti-microbial nano-structures, and (ii) with one or more anti-slip stripes, wherein the base layer comprises pre-aged elastic fibers that are pre-aged by elongation, the pre-aged elastic fibers exhibiting a fatigue behavior and providing the base layer with physical properties such that its stress-strain curve exhibits a lower and more consistent Young's modulus, at least over a working range of said stress-strain curve, compared to a base layer without pre-aged elastic fibers, the pre-aged elastic fibers calibrated to achieve 60-80 mm Hg of applied pressure after a pre-determined number of turns, and pre-aging allowing pressure exerted by the bandage to be a weak function of flexing and a strong function of the pre-determined number of turns;
   an application guide disposed on said base layer, wherein the application guide is arranged to attain a first geometrical shape when the base layer is stretched to a level falling within said working range of the stress-strain curve and to attain a second geometrical shape that differs from the first geometrical shape when the base layer is stretched to a level falling outside of said working range;
   an intermediate layer decorated with microbial and/or viral pathogen blocking structures; and
   a gauze and microbial cellulose that is decorated with anti-bleeding nano-structures.

* * * * *